United States Patent [19]

Zaborsky et al.

[11] 3,970,521

[45] July 20, 1976

[54] IMMOBILIZED GLYCOENZYMES

[75] Inventors: Oskar R. Zaborsky, Watchung, N.J.;
Allen I. Laskin, New York, N.Y.

[73] Assignee: Exxon Research and Engineering Company, Linden, N.J.

[22] Filed: Aug. 7, 1974

[21] Appl. No.: 495,339

[52] U.S. Cl.................................. 195/63; 195/68; 195/DIG. 11
[51] Int. Cl.².......................................... C07G 7/02
[58] Field of Search................. 195/63, 68, DIG. 11

[56] References Cited
UNITED STATES PATENTS

| 3,753,861 | 8/1973 | Forgione............................... 195/68 |
| 3,761,357 | 9/1973 | Epton et al. .......................... 195/63 |

FOREIGN PATENTS OR APPLICATIONS

| 83,154 | 8/1971 | Germany |

OTHER PUBLICATIONS

Zaborsky, O. Immobilized Enzymes, CRC Press, Cleveland, Ohio, 1973 (pp. 19, 29, 47, 59).

*Primary Examiner*—David M. Naff
*Attorney, Agent, or Firm*—Joseph J. Allocca; Robert J. Baran

[57] ABSTRACT

Glycoenzymes are immobilized by oxidizing a carbohydrate portion of the enzyme to a carbonyl group or a precursor thereof and reacting the resultant carbonyl group on the enzyme with an amino group of an amino-containing water insoluble polymer to produce a water insoluble conjugate. This method avoids loss of enzyme activity as a result of the carbohydrate portion of the enzyme which is catalytically inert being utilized in preparing the water-insoluble conjugate.

11 Claims, No Drawings

IMMOBILIZED GLYCOENZYMES

FIELD OF THE INVENTION

The instant invention relates to a method for immobilizing glycoenzymes, the products and uses thereof. In this invention, a glycoenzyme is treated with an oxidizing agent at conditions whereby carbonyl groups or their precursors, e.g., acetals, are formed in the carbohydrate portion of said glycoenzyme and the oxidized product thereafter contacted with an amino-containing material at conditions whereby a conjugate of the amino material and the glycoenzyme is formed. In a preferred embodiment of the instant invention, a glycoenzyme, e.g. glycose oxidase, is contacted with an aqueous periodic acid or sodium periodate solution at a pH of from 2.5 to 7.5 and a temperature of from about 5° to 40°C. for a time sufficient to convert a portion of the carbohydrate, to an oxidized product, i.e., one containing carbonyl or acetal groups. The oxidized glycoenzyme is then contacted with a water insoluble polymer, e.g., p-aminostyrene to form a water-insoluble conjugate of the glycoenzyme and the polymer. The most preferred enzyme-polymer conjugate, e.g., glucose oxidase and p-aminostyrene retains full activity when compared to a solution of glucose oxidase and shows enhanced thermal stability.

BACKGROUND OF THE PRIOR ART

Enzymes may be immobilized by a variety of chemical or physical techniques. Until now, all chemical techniques have involved the modification of the amino acid residues of an enzyme, even though the enzyme may have contained other functional groups which could be employed, e.g., the carbohydrate residues of glycoenzymes. Thus, glycoenzymes such as glucose oxidase or glucoamylase have been immobilized by chemical modification of only their amino acid residues. Recent work on the function of the carbohydrate residues of glucose oxidase has suggested that these sugar moieties are not involved in catalysis, thus it appears that it would be more desirable to covalently bond glycoenzymes to water-insoluble polymers by these catalytically nonessential carbohydrate groups than by amino acid groups, some of which are responsible for substrate binding and catalysis. This invention thus relates broadly to "non-amino acid immobilization" of enzymes.

The modification of glycoproteins with periodates is known in the art. For example, see Biochemical and Biophysical Research Communications, Vol. 31, No. 1, 1968 which teaches the modification of horseradish peroxidase by sodium metaperiodate to form an oxidized product. The author does not discuss the further reaction of this oxidized product to prepare, for example, an immobilized enzyme. Bossard, Annee Biol. 52, 202 (1948) teaches that periodic acid destroys the glucosidase of almonds. Similarly, Maekawa et al., Vol. 29, No. 7, at pages 353–356, Proc. Japan Acad. (1953) show the oxidation of alpha amylase with sodium metaperiodate to form an oxidized product which possesses only a small amount of its original activity. Again, oxidized alpha amylase was not suggested for further reaction nor as a precursor for an immobilized amylase composite.

In Archives of Biochemistry and Biophysics, 103, 515–518, 1963, Pazur et al. disclose periodate oxidation of alpha amylase and glucoamylase to obtain a product which has no loss in enzymatic activity. However, the authors did not suggest that this product could be further reacted to prepare an immobilized enzyme. Pazur et al. (Arch. Biochemistry and Biophysics, 111, 351–357 (1956)) teach the oxidation of the carbohydrate residue of glucose oxidase with sodium metaperiodate. The authors report that the enzyme loses activity after oxidation and do not suggest the further reaction of the oxidized product to prepare, for example, an immobilized glucose oxidase.

SUMMARY OF THE INVENTION

It has unexpectedly been discovered that immobilized glycoenzymes may be conveniently prepared by contacting a glycoenzyme with an oxidizing agent at conditions whereby the carbohydrate residue of glycoenzyme undergoes oxidation to form carbonyl groups or the precursors thereof and contacting this oxidized reaction product with an amino-containing material to form a water-insoluble conjugate of said amino-containing material and said oxidized glycoenzyme. Preferably, the amino-containing material is a polymer, for example, para-amino polystyrene. The preferred enzyme-polymer conjugates of the instant invention show activity substantially equal to the enzyme in its native state and show increased thermal stability.

Glycoenzymes are characterized as enzymes which have carbohydrate moieties as an integral part of the molecule. The role of the carbohydrate moieties in such an enzyme is not fully understood, but it has been suggested and somewhat substantiated that they are catalytically inert (i.e., not essential for activity). This invention takes advantage of the inertness of the carbohydrate moieties for catalysis to utilize them in binding the glycoenzyme to an amino-containing material to modify the enzyme and to form, for example, water-insoluble conjugates. Thus, this invention relates broadly to a method for making water-insoluble glycoenzymes, and the products and uses thereof.

Many glycoenzymes have been identified in the prior art. For example, see Pazur et al., *Advances in Carbohydrate Chemistry and Biochemistry*, Vol. 27, 1972, Academic Press, New York, beginning at page 301, herein incorporated by reference. The method of the instant invention may also be utilized to modify glycoproteins and glycopeptides in general. However, the instant method is especially suited to modifying glycoenzymes wherein a catalytically inert portion of the enzyme is utilized in preparing the water-insoluble conjugates. Thus, the problems inherent in many of the prior art processes for immobilizing enzymes, e.g., loss of activity may be avoided as a result of the bonding of the enzyme to a water-insoluble material through catalytically unnecessary groups.

This invention especially contemplates the immobilization of glucose oxidase, α-amylase, glucoamylase, invertase, galactosidase, bromelin, chloroperoxidase, peroxidase and various proteases. These enzymes may be used in the following processes: removal of $O_2$ from solutions (glucose oxidase); hydrolysis of starch (α-amylase, glucoamylase); hydrolysis of sucrose (invertase); hydrolysis of lactose (galactosidase); hydrolysis of peptides, amides and esters (bromelin); synthesis of carbon-halogen bonds (chloroperoxidase); oxidation of phenols, aminophenols, diamines and amino acids in the presence of $H_2O_2$ (peroxidase); and hydrolysis of proteins (proteases).

Various oxidizing agents may be used to oxidize the carbohydrate group of the glycoenzyme to carbonyl or carbonyl precursor groups, such as acetals. For example, lead tetraacetate, manganic acetate, cobaltic acetate, thallic acetate, ceric sulphate, etc., may be used. The preferred oxidizing agent, however, is a periodate, e.g., periodic acid, sodium metaperiodate, potassium metaperiodate, etc.

Oxidation of carbohydrates and polysaccharides with periodates is well known in the art. See, for example, J. M. Bobbitt, *Advances in Carbohydrate Chemistry*, 11, 1956 Academic Press, New York, beginning at page 1, herein incorporated by reference. In this article, the author discusses the use of various periodate compounds for oxidizing carbohydrate moieties. The techniques described are, in general, applicable to the preparation of oxidized glycoenzymes which are subsequently utilized in forming the immobilized glycoenzymes of the instant invention.

Preferably, the oxidized glycoenzyme is prepared by contacting the glycoenzyme with periodate in an aqueous solution at a pH of from 2.5 to 7.5, preferably from 4.5 to 6.5. The temperature during this contacting step is preferably maintained at from ca. 5° to 45°C., more preferably from 10° to 30°C. The glycoenzyme may be in a concentration of from 0.1 to 10 milligrams per milliliter, for example, about 2 milligrams per milliliter. The periodate concentration of the aqueous solution will be from about 0.1 to 5 milligrams per milliliter, for example, about 0.5 milligrams per milliliter. These conditions will be adjusted by the skilled artisan so as to obtain a glycoenzyme which is sufficiently oxidized, but still having sufficient activity for contacting with the amino-containing material in the subsequent step. The glycoenzyme is oxidized to form carbonyl groups or the precursors thereof, e.g., acetals which are used in the subsequent reaction with an amino compound.

It is known in the art that various glycoenzymes have varying amounts of carbohydrate attached thereto. In general, the periodate concentration is adjusted with regard to amount of glycoenzyme present and the amount of carbohydrate moiety present in the glycoenzyme.

Excess periodate based on the carbohydrate residues present is generally used, since the reaction generally does not go to completion. It is believed that some of the carbohydrate groups are sterically protected from the periodate, however, there are sufficient carbohydrate groups accessible for the formation of the carbonyl groups necessary for further reaction with the amino-containing material.

During the oxidation step, light is preferably excluded to prevent overoxidation of the glycoenzyme. A contact time sufficient to obtain at least a minimum concentration of carbonyl groups for the subsequent reaction with an amino-containing material is necessary. For example, the time of contacting the glycoenzyme with the periodate may range from 15 minutes to 24 hours, preferably from 30 to 180 minutes. The oxidized glycoenzyme is then preferably separated from the aqueous solution containing the remaining periodate. The oxidized glycoenzyme may be reacted with the amino-containing material without separation, provided that interfering compounds are absent, for example, compounds which react with amino groups or an excess of amino groups are present. The oxidized glycoenzyme may be conveniently separated by dialysis with a buffered solution. For example, an acetate buffer at a pH of 5.9 can be contacted across the membrane with the oxidized glycoenzyme solution until no further dialyzable material comes through. The oxidized glycoenzyme should be maintained at a temperature of less than 25°C. if it is to be stored prior to the subsequent coupling step.

An aqueous solution of the oxidized glycoenzyme, e.g., from 0.1 to 3% glycoenzyme is then contacted with the amino-containing material. Preferably the amino-containing material is a water-insoluble material, e.g., a polymer, but low molecular weight amino-containing compounds may also be utilized. The pH during this contacting step is adjusted to be either slightly acidic or basic, preferably from 5.5 to 6.5 or 7.5 to 9.5. Either HCl or NaOH may be conveniently used to adjust the pH. The mixture is stirred at a temperature of from 5° to 35° for a time sufficient to form the glycoenzyme-amino conjugate. The conjugate may be then separated from the mixture by filtration and is preferably washed sequentially with water and salt solution, e.g., buffered sodium chloride to remove any nonbonded enzyme.

The amino-containing material is utilized in the method of the instant invention contains at least one amino group per molecule. Preferably the amino-containing material has at least one primary amine. Secondary amino groups are less preferred for reaction with the oxidized glycoenzyme, while tertiary amino groups are least preferred.

The amino group is selected so that the resulting enzyme-amine conjugate, after reaction, is water-insoluble. Preferably the conjugate is a water-insoluble solid material and can be utilized in enzyme catalyzed reactions in a heterogeneous manner. Amines containing more than one amino group, especially primary amino groups, are preferred.

The amino compound used in the process of the instant invention may be selected from compounds having the general formula:

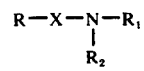

wherein R, $R_1$, and $R_2$ are selected from the group consisting of hydrogen, hydrocarbyl and substituted hydrocarbyl radicals, and X is a nitrogen or carbon atom. The substituents present in the hydrocarbyl radicals may contain halogen, oxygen, sulfur, phosphorous, silicon and nitrogen.

Preferably R is an essentially linear chain, polymeric moiety, e.g., having a molecular weight of from 500 to 1 million, and $R_1$ and $R_2$ are hydrogen. When X is nitrogen there will be another group covalently attached thereto, which is not represented in the general formula given above. When X is carbon, of course, there will be two nonrepresented, covalently attached groups. Generally, these groups will be hydrogen or hydrocarbyl groups, e.g., having up to 20 carbon atoms. Preferably these groups are hydrogen and $C_1$ to $C_3$ alkyl groups, most preferably hydrogen groups.

Certain of the substituents described above when present in the preferred R group, i.e., the polymeric moiety, may be pendant from the polymer chain or present as hereto atoms therein. For example, oxygen substituents may be present in a hereto ether form, e.g., R may be a polyethylenoxide radical; or as a pendant carbonyl group, e.g., R may be a polyvinylacetate radical.

Preferably the amino-containing material is a water-insoluble amino-containing polymer, e.g., poly-p-aminostyrene, aminoethylcellulose, carboxymethylcellulose hydrazide, Biogel P-2 hydrazide, which is a derivative of polyacrylamide, available from Bio-Rad Corp., Richmond, Calif. amino-Sepharose which may be prepared according to the procedure described by Cuatrecasas, J. Biol. Chem., 245, 3059–3065 (1970) amino alkylated glass, available from Pierce Chemical, Rockford, Ill., etc.

It has been found surprisingly that the glycoenzymepoly p-aminostyrene conjugate of the instant invention shows activity substantially equivalent to the glycoenzyme in its native state, i.e., in aqueous solution. More surprisingly, it has been found that many of the glycoenzyme amino polymer conjugates show enhanced thermal stability when compared to the native enzymes.

The water-insoluble conjugate of the instant invention may be used in all the processes wherein the native glycoenzymes are now used. Furthermore advantage may be taken of the increased thermal stability to run these processes at higher temperatures without encountering denaturation of the enzyme.

The following are specific embodiments of the instant invention.

EXAMPLE 1

Glucose oxidase from *Aspergillus niger* (Worthington Biochemical Corp., Freehold, N.J.) was measured spectrophotometrically for activity at 460 nm by the coupled peroxidase-o-dianisidine system using D-glucose in 100 mM phosphate buffer, pH 6.0 at 25° See Weetall, H. H. and Hersh, L. S. (1970) Biochim. Biophys. Acta 206, 54–60. The activity of immobilized enzyme derivatives was determined as described in Zaborsky, O. and Ogletree, J. (1972) Biochim. Biophys. Acta 209, 68–76.

The concentration of glucose oxidase was determined spectrophotometrically at 450 nm (50 mM acetate buffer, pH 5.6) using the extinction coefficient of $1.41 \times 10^4$ $M^{-1}$ $cm^{-1}$. The concentration of catalytically active enzyme was determined spectrophotometrically using the differential molar extinction coefficient at 450 nm of $1.31 \times 10^4$ $M^{-1}$ $cm^{-1}$. See Weibel, M. K. and Bright, H. J. (1971) J. Biol. Chem. 246, 2734–2744. The concentration of catalytically active enzyme was determined spectrophotometrically using the differential molar extinction coefficient at 450 nm of $1.31 \times 10^4$ $M^{-1}$ $cm^{-1}$ by anaerobic titration of the enzyme with glucose. See Weibel, M. K. and Bright, H. J. (1971) Biochem. J. 124, 801–807. Protein content of enzyme polymer conjugates was determined by amino acid analysis using the described procedure. See Zaborsky, O. R. and Ogletree, J. (1972) Biochim. Biophys. Acta 289, 68–76. The amount of protein was determined from the amount of alanine (Ala), valine (Val), and glutamic acid (Glu) found and by assuming that the mole weight of the enzyme is 150,000 and that there are 108 Ala, 79 Val, and 99 Glu residues per molecule. See Pazur, J. H., Kleppe, K., and Cepure, A. (1965) Arch. Biochem. Biophys. 111, 351–357.

Oxidation of Glucose Oxidase with Periodic Acid

To a stirred solution of glucose oxidase (40.2 mg, $2.68 \times 10^{-7}$ mole, in 20 ml 50 mM acetate buffer, pH 5.60) in a thermostated vessel at 25° protected from light was added 0.4 ml of a periodic acid solution (9.12 mg, $4.00 \times 10^{-5}$ mole). The yellow solution was stirred for 4 hours upon which 0.025 ml of ethylene glycol, $4.48 \times 10^{-4}$ mole, was added to react with excess periodate and stirred for an additional 0.5 hour. The solution was transferred to an Amicon Model 202 ultrafiltration cell equipped with an XM-50 filter at 50 psi $N_2$ pressure and dialyzed with 50 mM acetate buffer, pH 5.59, until no further dialyzable material came forth. The conversion of periodic acid after the 4 hours of reaction with glucose oxidase, based on the absorbance change at 223 nm Dixon, J. J. and Lipkin, D. (1954) Anal. Chem. 26, 1092–1093, was 61.6%. The oxidized enzyme was stored at 5°.

Coupling of Oxidized Glucose Oxidase to p-Aminostyrene

To a 5 ml. solution of oxidized glucose oxidase (10 mg) was added 250 mg finely powdered p-aminostyrene which is available from Polysciences Inc., Warrington, Pa. The suspension was adjusted to pH 9 with 0.1 N NaOH, stirred at ca. 25° for 1 hour and then filtered with a Millipore 0.45$\mu$ filter. The solid was washed with 1 l. of $H_2O$ and 1 l. of 1 M NaCl in 50 mM phosphate buffer, pH 6.4. After several ml of the $H_2O$ wash, no further activity was detected in the wash. The original filtrate exhibited high activity; the NaCl wash exhibited no activity.

Coupling of oxidized glucose oxidase with p-aminostyrene resulted in an active enzyme-polymer conjugate. While not wishing to be bound by theory it is presumed that the enzyme is bound to the polymers through an imine linkage. However, when the amino-containing material is a hydrazide, the linkage is a hydrazone. The protein loading (mg of enzyme per g of enzyme-polymer conjugate) with the p-aminostyrene is 5 to 8 mg. The activity of the immobilized enzyme is equivalent to the native and oxidized enzymes. See Table I below. It is likely that this is due to immobilizing the enzyme via catalytically nonessential carbohydrate residues for no amino acid residues were found to be oxidized in the enzyme.

The conjugate was stored for 6 weeks in 100 mM phosphate buffer, pH 6.31. The conjugate retained its activity and the buffer remained inactive, thus showing no desorption.

Table 2 shows the thermal stability of the glucose oxidase. It is noted that the native and oxidized enzymes have similar stabilities (the oxidized enzyme exhibiting slightly more stability), whereas the water-insoluble conjugate has definite enhanced stability. Other amino-containing polymers (aminoethylcellulose, carboxymethylcellulose hydrazide, Biogel P-2 hydrazide and amino-Sepharose) were also employed for immobilizing oxidized glucose oxidase. See Table III for these results.

The enzyme-polymer conjugates were tested for thermal stability at 60°C. as an aqueous suspension or solution (native enzyme) in a sodium acetate buffer at pH 5.6. The concentration of native and oxidized enzyme was adjusted to 0.4 mg/ml. The concentration of conjugate was ca. 0.75 mg/ml.

TABLE I

Specific Activities of Glucose Oxidases

| Glucose Oxidase | Specific Activity (units/mg protein) |
|---|---|
| Native | 91.9[a] |
| Oxidized | 92.5[a] |
| p-aminostyrene-bound | 93.1[b] |

[a]Based on protein as determined by anaerobic spectral titration with glucose.
[b]Based on protein as determined by amino acid analysis. Protein loading was 5.87 mg enzyme/g of enzyme-polymer conjugate.

TABLE II

Thermal Stability
Relative Activity of Glucose Oxidases
(Percent)

| Time (Hours) | Native | Oxidized | p-aminostyrene-Conjugate |
|---|---|---|---|
| 0 | 100 | 100 | 100 |
| 0.25 | 63.4 | 76.0 | 76.8 |
| 0.50 | 47.1 | 59.1 | 60.0 |
| 0.75 | 36.8 | 49.3 | 59.4 |
| 1.0 | 27.4 | 38.1 | 56.6 |
| 1.5 | 15.7 | 30.0 | 48.1 |
| 2.0 | 8.7 | 21.0 | 41.4 |
| 3.0 | 3.5 | 11.0 | 34.5 |
| 4.0 | 1.8 | 6.4 | 28.6 |
| 5.0 | 1.1 | 4.0 | 24.6 |
| 6.0 | 0 | 2.7 | 24.3 |
| 48.0 | — | — | 12.7 |

TABLE III

Thermal Stability of Glucose Oxidase - Bio-Gel P-2
Hydrazide Conjugate

| Time (Hours) | Relative Activity (Percent) |
|---|---|
| 0 | 100 |
| 0.5 | 96.7 |
| 1.0 | 78.9 |
| 1.5 | 64.0 |
| 2.0 | 64.4 |
| 2.5 | 66.7 |
| 3.0 | 51.7 |
| 24.0 | 27.2 |
| 53.0 | 12.1 |
| 68.0 | 5.4 |
| 92.0 | 4.4 |

Thermal Stability of Glucose Oxidase
Amino-Sepharose Conjugate

| Time (Hours) | Relative Activity (Percent) |
|---|---|
| 0 | 100 |
| 0.5 | 85.2 |
| 1.0 | 93.8 |
| 1.5 | 76.7 |
| 2.0 | 85.0 |
| 2.5 | 86.1 |
| 3.0 | 71.7 |

EXAMPLE 2

Coupling and Chromatography of Oxidized Glucose Oxidase on Aminoethyl (AE)-Cellulose To a column of AE-cellulose (Bio-Rad Cellex-AE, 0.25 mg/g exchange capacity) (0.9 cm diameter × 12.5 cm length) previously washed with 100 ml 5 M NaCl-50 mM sodium acetate buffer, pH 4.93, and with 100 ml of 50 mM sodium acetate buffer, pH 4.94 (at 40 ml/hr using a precision-metering pump) was applied 1.0 ml of native or oxidized glucose oxidase. One ml portions were collected and the absorbance at 280 nm was monitored. After 30 ml had passed, the buffer was changed from 50 mM sodium acetate, pH 4.93 to 1 M NaCl-50 mM acetate, pH 4.94 to 2.5 M NaCl-50 mM acetate, pH 4.94 to 5 M NaCl-50 mM acetate, pH 4.94. After elution with the 5 M NaCl-buffer, the column was washed with 50 mM acetate buffer, pH 4.93. Separate, but identical, columns were used for native and oxidized glucose oxidase. At the end of the elution, activity was observed in both AE-cellulose columns (activity being found on the top as well as the bottom of the packed-bed).

The results are given in Table IV below. Note that the oxidized enzyme is recoverable during elution in a much lesser amount, thus indicating that a water-insoluble enzymeamino polymer conjugate is formed.

The oxidized enzyme-amino polymer conjugate was tested for activity and shown to have an increased activity over the enzyme in its native state.

TABLE IV

Chromatography and Coupling of Native and Oxidized Glucose Oxidase on AE-Cellulose

| | Native G.O. | Ox. G.O. |
|---|---|---|
| Mg of Protein Applied | 2.94 | 2.67 |
| Mg of Protein Recovered (Soluble) | 2.54 | 0.84 |
| % Recovery | 86.4% | 31.5% |
| Mg of Protein Not Recovered (on AE-cell.) | 0.40 (diff.) | 1.83 (by diff.) |

EXAMPLE 3

Coupling of Oxidized Glucose Oxidase to Carboxyl Methyl Cellulose (CMC)-Hydrazide Oxidized glucose oxidase was coupled to the hydrazide of carboxymethylcellulose (Enzite, CMC-hydrazide) available from Miles Laboratories, Elkhardt, Ind., by a similar procedure as used for polyaminostyrene. Conditions for the coupling were: 250 mg Enzite and 10.2 mg oxidized glucose oxidase were contacted in 10 ml of an aqueous acetate buffer solution at a pH 5.06 for 18 hours at 5°. Washing of the enzyme-polymer conjugate presented problems due to clumping — a problem which was not present in the control (glucose oxidase and CMC-hydrazide). The conjugate was washed with 130 ml 50 mM sodium acetate at a pH 4.94, and with 600 ml in NaCl in 50 mM sodium acetate buffer, pH 4.8 until clean of activity (of filtrate, ca. 150 ml). The solid was active and stored in the buffer at 5°.

The control solid, similar to PAS, also possessed only a slight amount of activity.

EXAMPLE 4

Coupling of Glucose Oxidase to the Hydrazide of Bio-gel P-2

Coupling of oxidized glucose oxidase to the hydrazide Bio-gel P-2 (100–200 mesh) was performed in 50 mM sodium acetate, pH 5.51 for 19 hours at 5°. A corresponding control using native glucose oxidase was also run. Washing of the conjugates was accomplished with 50 mM sodium acetate buffer, pH 5.6 and 1 M NaCl-50 mM sodium acetate, pH 5.8 and 2.0 M NaCl-50 mM acetate, pH 5.1. Contrary to the oxidized glucose oxidase, all activity could be removed from the hydrazide-native G.O. conjugate by the 2 M NaCl wash (the adsorbed enzyme).

What is claimed is:

1. A water-insoluble enzyme-polymer conjugate, comprising a glycoenzyme covalently bound to an amino-containing water-insoluble polymer through a hydrazone linkage between a carbonyl group on the enzyme and an amino group on the amino-containing water insoluble polymer.

2. The conjugate of claim 1 wherein said enzyme is glucose oxidase.

3. The conjugate of claim 1 wherein said polymer is a polyacrylamide derivative.

4. The conjugate of claim 1 wherein said polymer is a carboxy methylcellulose derivative.

5. A method for immobilizing a glycoenzyme which comprises oxidizing the carbohydrate portion of the glycoenzyme at conditions whereby at least one carbonyl group or acetal group is formed and coupling the oxidized glycoenzyme to an amino-containing water-insoluble material by reacting a carbonyl group of the glycoenzyme with an amino group of the water-insoluble material to cause coupling of the glycoenzyme to the water-insoluble material through a hydrazone or imine linkage to produce a water-insoluble immobilized glycoenzyme-amino conjugate.

6. A method for immobilizing a glycoenzyme which comprises contacting the glycoenzyme with a periodate containing material at conditions whereby the carbohydrate portion of the enzyme is oxidized to form at least one carbonyl group or acetal group, separating the oxidized glycoenzyme from said periodate containing material, coupling the oxidized glycoenzyme to an amino-containing water-insoluble polymer by reacting a carbonyl group of the glycoenzyme with an amino group of the water-insoluble polymer to cause coupling of the glycoenzyme to the polymer through a hydrazone or imine linkage to produce a water-insoluble immobilized glycoenzyme.

7. The process of claim 6 wherein said glycoenzyme is glucose oxidase.

8. The process of claim 6 wherein said water-insoluble polymer is para-aminostyrene.

9. The process of claim 7 wherein said periodate is contacted with said glycoenzyme in an aqueous solution at a pH of from 2.5 to 7.5.

10. The process of claim 9 wherein said periodate is selected from the group consisting of periodic acid and sodium periodate.

11. The process of claim 10 wherein the temperature of contact ranges from about 5° to about 45°C.

* * * * *